United States Patent
Hong et al.

(10) Patent No.: US 12,262,992 B2
(45) Date of Patent: Apr. 1, 2025

(54) METHOD OF ESTIMATING HEMOGLOBIN CONCENTRATION USING SKIN IMAGE OR HEALTH INFORMATION AND BODY INFORMATION AND HEMOGLOBIN CONCENTRATION ESTIMATING APPARATUS PERFORMING THE METHOD

(71) Applicant: Research & Business Foundation SUNGKYUNKWAN UNIVERSITY, Suwon-si (KR)

(72) Inventors: Kwang Seok Hong, Suwon-si (KR); Jin Soo Park, Suwon-si (KR); Sang Hoon Hong, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 335 days.

(21) Appl. No.: 17/732,923

(22) Filed: Apr. 29, 2022

(65) Prior Publication Data

US 2022/0346678 A1    Nov. 3, 2022

(30) Foreign Application Priority Data

Apr. 30, 2021    (KR) .................. 10-2021-0056314

(51) Int. Cl.
*A61B 5/145*    (2006.01)
*A61B 5/103*    (2006.01)
(Continued)

(52) U.S. Cl.
CPC ........ *A61B 5/14546* (2013.01); *A61B 5/1032* (2013.01); *A61B 5/1455* (2013.01);
(Continued)

(58) Field of Classification Search
CPC . A61B 5/14546; A61B 5/1032; A61B 5/1455; G06T 7/90; G06T 7/0012;
(Continued)

(56) References Cited

U.S. PATENT DOCUMENTS

| | | | |
|---|---|---|---|
| 2010/0185064 A1* | 7/2010 | Bandic ................ | A61B 5/444 600/306 |
| 2022/0003671 A1* | 1/2022 | Ghosh ................. | G01N 21/293 |
| 2022/0262148 A1* | 8/2022 | Lee ...................... | G06N 20/00 |

FOREIGN PATENT DOCUMENTS

| | | |
|---|---|---|
| JP | 2018-102730 A | 7/2018 |
| KR | 10-2016-0092013 A | 8/2016 |
| WO | WO 2015-084462 A1 | 6/2015 |

OTHER PUBLICATIONS

Galeano, July A., et al. "Quantification of melanin and hemoglobin in human skin from multispectral image acquisition: use of a neuronal network combined to a non-negative matrix factorization." Applied and Computational Mathematics 11.2 (2012): 1-14.
(Continued)

*Primary Examiner* — John J Lee
(74) *Attorney, Agent, or Firm* — NSIP Law (57) ABSTRACT

A method of estimating hemoglobin concentration, may comprise: receiving a skin image of a subject; determining a formula into which the skin image is introduced; and estimating a hemoglobin concentration of the subject by introducing the skin image into the determined formula.

17 Claims, 7 Drawing Sheets

(51) Int. Cl.
  *A61B 5/1455* (2006.01)
  *G06T 7/00* (2017.01)
  *G06T 7/90* (2017.01)
  *G16H 10/60* (2018.01)
  *G16H 30/40* (2018.01)

(52) U.S. Cl.
  CPC .............. *G06T 7/0012* (2013.01); *G06T 7/90* (2017.01); *G16H 10/60* (2018.01); *G16H 30/40* (2018.01); *G06T 2207/10024* (2013.01); *G06T 2207/30088* (2013.01); *G06T 2207/30101* (2013.01)

(58) Field of Classification Search
  CPC . G06T 2207/10024; G06T 2207/30088; G06T 2207/30101; G16H 10/60; G16H 30/40
  See application file for complete search history.

(56) References Cited

OTHER PUBLICATIONS

Korean Office Action issued on Nov. 24, 2022, in counterpart Korean Patent Application No. 10-2021-0056314 (6 pages in English, 5 pages in Korean).

\* cited by examiner

METHOD OF ESTIMATING HEMOGLOBIN CONCENTRATION USING SKIN IMAGE OR HEALTH INFORMATION AND BODY INFORMATION AND HEMOGLOBIN CONCENTRATION ESTIMATING APPARATUS PERFORMING THE METHOD

FIELD

The present disclosure relates to a method of estimating hemoglobin concentration using skin image or health information and body information and a hemoglobin concentration estimating apparatus performing the method.

BACKGROUND

Hemoglobin (or haemoglobin) is an iron-containing protein in the red blood cells that carries oxygen throughout the body. A lack of iron, which is one of the components of hemoglobin, can cause hemoglobin to stop functioning completely and lead to anemia.

Hemoglobin is present mostly in the red blood cells. An abrupt decrease in hemoglobin concentration in patients with anemia may result in fatal effects such as death, and it is thus necessary to do regular monitoring of their hemoglobin concentration. It is important, especially for pregnant women or surgery patients, to constantly monitor their hemoglobin concentration because they are vulnerable to abrupt changes in hemoglobin concentration.

Conventionally, hemoglobin concentration measurement was done usually by hemoglobin measurement using blood sampling and hemoglobin measurement using light scattering.

The hemoglobin measurement using blood sampling is a method of measuring hemoglobin concentration using microneedles, which is a minimally invasive technique that involves pain from blood drawing.

In the hemoglobin measurement using light scattering, hemoglobin concentration is measured using a hemoglobin analyzer. Hemoglobin analyzers are one of the most widely used instruments for measuring hemoglobin concentration in blood, and are often used in hospitals, clinics, or large laboratories. The hemoglobin analyzers require 50 to 200 µl of blood to measure hemoglobin concentration each time and have relatively very high accuracy, but one drawback with them is that it takes 30 seconds to measure hemoglobin concentration. Moreover, the hemoglobin analyzers are expensive and involve high costs of measurement, and are not appropriate for regular monitoring of the general public, day patients, or outpatients because of their large volume and heavy weight. Besides, they are less accessible to the general public with the exception of trained professionals, and require the use of potassium cyanide for each measurement which is a toxic compound.

Meanwhile, hemoglobin reversibly binds to oxygen molecules and carries oxygen to the cells and the tissues, and hemoglobin appears red when bound to sufficient oxygen, whereas hemoglobin not bound to oxygen appears blue. As a consequence, hemoglobin gives the skin of a healthy person a rosy, healthy-looking color, but makes the skin of an unhealthy person look bluish and pale due to the lack of oxygen.

Moreover, in the case of the face and neck where capillaries lie adjacent to the skin surface, the red color of hemoglobin greatly affects the skin color.

Therefore, in order to provide non-contact hemoglobin measurement techniques that allow for easy measurement and can be used anywhere at any time, there is a need to develop a method of estimating hemoglobin using a user's body and health information or a method of measuring hemoglobin in a non-contact manner using a camera the user owns, including a regular camera, an infrared camera, a zoom camera, etc.

SUMMARY

In view of the above, the present disclosure provides a method of estimating hemoglobin concentration using skin image or health information and body information.

The aspects of the present disclosure are not limited to the foregoing, and other aspects not mentioned herein will be clearly understood by those skilled in the art from the following description.

In accordance with an aspect of the present disclosure, there is provided a method for estimating hemoglobin concentration, the method comprising: receiving a skin image of a subject; determining a formula into which the skin image is introduced; and estimating a hemoglobin concentration of the subject by introducing the skin image into the determined formula.

The method may comprise upon receiving the skin image, detecting from the skin image at least one region of interest including a body region of the subject where veins are visible; converting color space of the at least one region of interest; and calculating an average color value and an average saturation value with respect to the at least one region of interest The may comprise estimating the hemoglobin concentration of the subject including estimating the hemoglobin concentration by introducing at least one of the average color value and the average saturation value into the determined formula.

The method may comprise receiving at least one of health information and body information of the subject.

The determining the formula into which the skin image is introduced includes determining the formula by using at least one of the skin image and the health information and body information.

The estimating the hemoglobin concentration of the subject includes estimating the hemoglobin concentration by determining whether to classify the health information and the body information and introducing the health information and the body information into a formula corresponding to a classification criterion.

The estimating the hemoglobin concentration of the subject includes, in a case where the health information and the body information are not classified, estimating the hemoglobin concentration by applying a regression analysis equation corresponding to the whole of the health information and the body information.

The estimating the hemoglobin concentration of the subject includes, in a case where the health information and the body information are classified according to either the sex, smoking status, or age range indicated in the health information or the body information, estimating the hemoglobin concentration of the subject by introducing the health information and the body information into a formula for the indicated sex, smoking status, or age range. The estimating the hemoglobin concentration of the subject includes: estimating a first hemoglobin concentration by introducing the skin image into a first hemoglobin concentration estimation formula corresponding to the skin image; estimating a second hemoglobin concentration by introducing the first hemoglobin concentration into a second hemoglobin concentration estimation formula for the skin image; estimating a third hemoglobin concentration by introducing the health information and the body information into a health information and body information-based hemoglobin concentration estimation formula corresponding to the health information and the body information; and estimating an integrated hemoglobin concentration by calculating a weighted sum of two or more of the first hemoglobin concentration, the second hemoglobin concentration, and the third hemoglobin concentration. In accordance with another aspect of the present disclosure, there is provided an apparatus for estimating hemoglobin concentration, the apparatus comprising: a memory storing a hemoglobin concentration estimation program; and a processor configured to execute the hemoglobin concentration estimation program by loading the hemoglobin concentration estimation program from the memory, wherein the processor executes the hemoglobin concentration estimation program configured to receive a skin image of a subject, determine a formula into which the skin image is introduced, and estimate the hemoglobin concentration of the subject by introducing the skin image into the formula.

In accordance with another aspect of the present disclosure, there is provided a non-transitory computer-readable recording medium storing a computer program, which comprises instructions configured for a processor to execute a method of estimating hemoglobin concentration, the method comprising: receiving a skin image; determining a formula into which the skin image is introduced; and estimating the hemoglobin concentration of the subject by introducing the skin image into the determined formula.

According to embodiments of the present disclosure, the present disclosure allows easy estimation of hemoglobin concentration with high accuracy, by estimating hemoglobin concentration using skin image or health information and body information.

DETAILED DESCRIPTION

The advantages and features of the present disclosure and the methods of accomplishing these will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

In describing the embodiments of the present disclosure, if it is determined that detailed description of related known components or functions unnecessarily obscures the gist of the present disclosure, the detailed description thereof will be omitted. Further, the terminologies to be described below are defined in consideration of functions of the embodiments of the present disclosure and may vary depending on a user's or an operator's intention or practice. Accordingly, the definition thereof may be made on a basis of the content throughout the specification.

Figure 1:
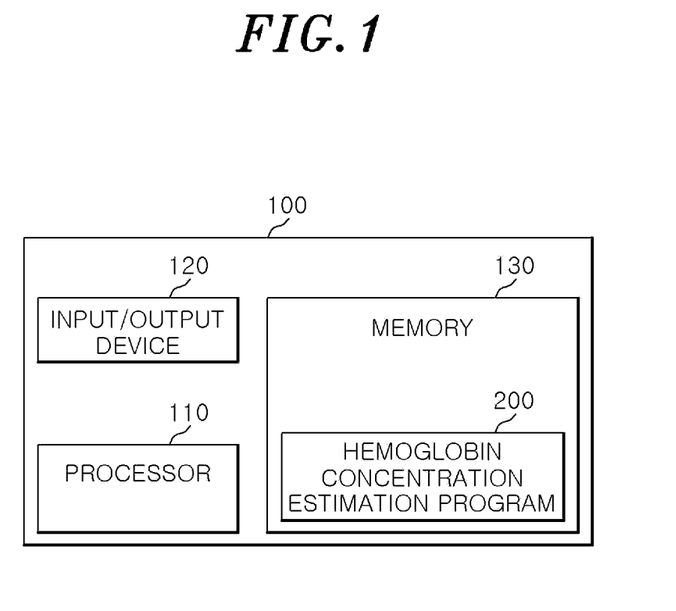
FIG. 1 is a block diagram showing a hemoglobin concentration estimation apparatus according to an embodiment of the present disclosure.

FIG. 1 is a block diagram showing a hemoglobin concentration estimation apparatus according to an embodiment of the present disclosure.

Referring to FIG. 1, the hemoglobin concentration estimation apparatus 100 may include a processor 110, an input/output device 120, and a memory 130.

The processor 110 may control the overall operation of the hemoglobin concentration estimation apparatus 100.

The processor 110 may receive an input of at least one of a time of eating, skin image, health information, and body information, using the input/output device 120.

Although the time of eating, the skin image, the health information, and the body information as described herein are inputted through the input/output device 120, they are not limited to this. That is, in some embodiments, the hemoglobin concentration estimation apparatus 100 may include a transceiver (not shown), and hemoglobin concentration estimation apparatus 100 may receive an input of at least one of a time of eating, skin image, health information, and body information, using the transceiver (not shown), and at least one of the time of eating, the skin image, the health information, and the body information may be generated in the hemoglobin concentration estimation apparatus 100.

Here, the skin image is a captured image of the face, hands, etc. of a person (subject), which may refer to an image from which hemoglobin concentration can be estimated by analyzing veins in the skin based on the average color and saturation of a skin image.

Furthermore, the body information may include sex, age, height, weight, and waist size, and the health information may include diastolic blood pressure, triglyceride, serum GOT (ALT), gamma GTP, and smoking status.

The processor 110 may estimate the hemoglobin concentration of a person by using at least one of input skin image, health information, and body information.

The input/out device 120 may include one or more input devices and/or one or more output devices. For example, the input devices may include a microphone, a keyboard, a mouse, a touchscreen, etc., and the output devices may include a display, a speaker, etc.

The memory 130 may store a hemoglobin concentration estimation program 200 and information needed to execute the hemoglobin concentration estimation program 200.

In the present disclosure, the hemoglobin concentration estimation program 200 may refer to software that includes instructions for receiving an input of at least one of skin image, body information, and health information of a person and estimating the hemoglobin concentration of the person.

In order to execute the hemoglobin concentration estimation program 200, the processor 110 may load from the memory 130 the hemoglobin concentration estimation program 200 and information needed to execute the hemoglobin concentration estimation program 200.

The processor 110 may estimate the hemoglobin concentration of a person by executing the hemoglobin concentration estimation program 200. Functions and/operation of the hemoglobin concentration estimation program 200 will be described in detail with reference to FIG. 2.

Figure 2:
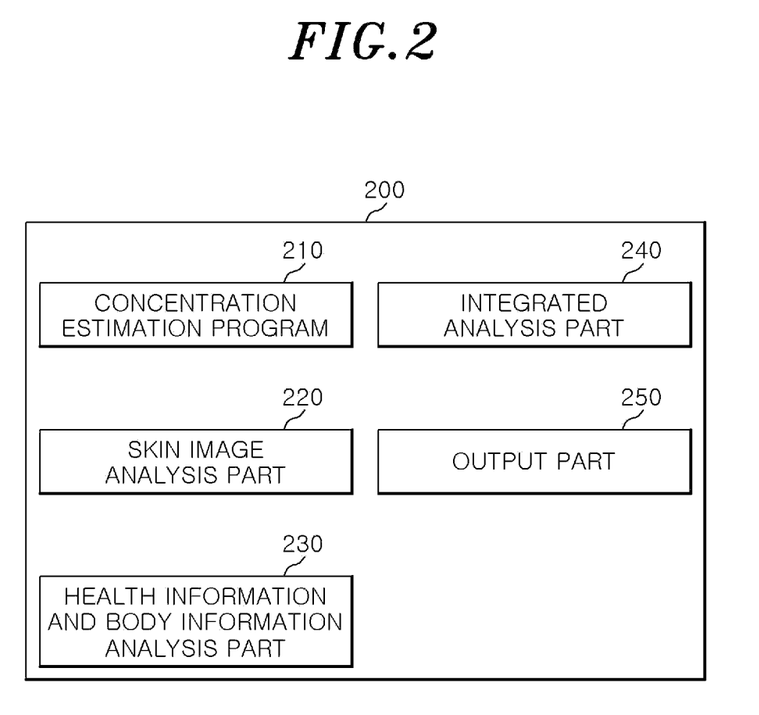
FIG. 2 is a block diagram conceptually showing functions of a hemoglobin concentration estimation program according to an embodiment of the present disclosure.

FIG. 2 is a block diagram conceptually showing functions of a hemoglobin concentration estimation program according to an embodiment of the present disclosure.

Referring to FIG. 2, the hemoglobin concentration estimation program 200 may include an estimation method selection part 210, a skin image analysis part 220, a health information and body information analysis part 230, an integrated analysis part 240, and an output part 250.

The estimation method selection part 210, skin image analysis part 220, health information and body information analysis part 230, integrated analysis part 240, and output part 250 illustrated in FIG. 2 are functions of the hemoglobin concentration estimation program 200 that are conceptually distinguished from one another to easily explain the functions of the hemoglobin concentration estimation program 200, but are not limited to them. In some embodiments, the functions of the estimation method selection part 210, the skin image analysis part 220, the health information and body information analysis part 230, the integrated analysis part 240, and the output part 250 may be combined together or separated from one another, and may be implemented by a series of instructions included in one program.

The estimation method selection part 210 may select the method of estimating the hemoglobin concentration of a person according to a user's input.

More specifically, the estimation method selection part 210 may select any method from among skin image analysis, health information and body information analysis, skin image and sex-based analysis, and integrated analysis.

The skin image analysis is a method of analysis that estimates the hemoglobin concentration of a person based on input skin image, the health information and body information analysis is a method of analysis that estimates the hemoglobin concentration of a person based on the person's input health information, the skin image and sex-based analysis is a method of analysis that estimates the hemoglobin concentration of a person based on the person's skin image and sex, and the integrated analysis is a method of analysis that estimates the concentration of a person based on two or more of the person's skin image, sex, health information, and body information.

If the estimation method selection part 210 selects the skin image analysis, the skin image analysis part 220 may estimate the hemoglobin concentration of a person based on the person's input skin image.

To this end, the skin image analysis part 220 may detect at least one region of interest (ROI) from the skin image.

In some embodiments, the skin image analysis part 220 includes an artificial neural network that is trained to detect a region of interest in the skin from the skin image, and may detect at least one region of interest from the skin image by using the artificial neural network.

The skin image analysis part 220 may convert the color system of the detected region of interest in the skin. For example, if the skin image is created using an RGB color system, the skin image analysis part 220 may convert the color system of the region of interest to a YCbCr color system.

The skin image analysis part 220 may calculate the average of blue color values in the RGB color system, the average of Cb color values in the YCbCr color system, and the average saturation, with respect to the at least one detected region of interest.

The skin image analysis part 220 may estimate hemoglobin concentration by introducing at least one of the average of blue color values, the average of Cb color values, and the average saturation into a regression analysis formula for estimating a first hemoglobin concentration.

Although the skin image analysis part 230 as described herein estimates hemoglobin concentration by using a blue color value and a Cb color value, the present disclosure is not limited to this. That is, in some embodiments, the skin image analysis 230 may estimate hemoglobin concentration by using other colors (for example, red or Cr), as well as blue and Cb.

In this instance, the regression analysis formula for estimating the first hemoglobin concentration may include a plurality of regression analysis formulae, and the skin image analysis part 220 may determine which regression analysis formula to use in estimating hemoglobin concentration, among the plurality of regression analysis formulae, based on which type of data is used in estimating hemoglobin concentration among the average of blue color values, the average of Cb color values, and the average saturation, when was the last time the person ate their meal (prior to analysis), and the type of regression analysis formula.

Here, the type of regression analysis formula may include a linear regression formula, a curve regression formula, and a multiple regression formula, and the skin image analysis part 220 may determine whether the current state is before meal or after meal (or one of before breakfast, after breakfast, before lunch, after lunch, before dinner, and after dinner), based on the difference between the time of eating and the current time.

For example, if the current state is before breakfast, the average of blue color values is used, and a linear regression formula is used as a regression analysis formula, the skin image analysis part 220 may estimate hemoglobin concentration by using a before breakfast-blue linear regression formula. On the other hand, if the current state is after lunch, the average saturation is used, a curve regression formula is used as a regression analysis formula, the skin image analysis part 220 may estimate hemoglobin concentration by using an after lunch-saturation curve regression formula.

Table 1 below shows an example of regression analysis formulae included in the first skin image regression analysis formula.

TABLE 1

| | Classification | | | Regression analysis formula |
|---|---|---|---|---|
| Breakfast | Before meal | Linear | B | $y = 0.0585x + 8.4347$ |
| | | | Cb | $y = -0.2297x + 41.332$ |
| | | | S | $y = -7.1456x + 18.154$ |
| | | Curve | B | $y = -0.0023x^2 + 0.6128x - 24.382$ |
| | | | Cb | $y = 0.0273x^2 - 6.3668x + 385.83$ |
| | | | S | $y = 378.05x^2 - 279.53x + 67.056$ |

TABLE 1-continued

| Classification | | | | Regression analysis formula |
|---|---|---|---|---|
| | | Multiple regression | | $y = 0.0579x_1 - 0.0649x_2 + 2.4173x_3 + 14.9093$ |
| | After meal | Linear | B | $y = 0.1121x + 14.207$ |
| | | | Cb | $y = +0.285x + 46.311$ |
| | | | S | $y = -24.555x + 23.382$ |
| | | Curve | B | $y = 0.0029x^2 - 0.5877x + 43.197$ |
| | | | Cb | $y = -2.7359x^2 + 611.24x - 34124$ |
| | | | S | $y = -416.04x^2 + 269.82x - 28.515$ |
| | | Multiple regression | | $y = 0.1228x_1 + 0.0597x_2 + 9.9665x_3 - 10.0426$ |
| Lunch | Before meal | Linear | B | $y = 0.0139x + 12.834$ |
| | | | Cb | $y = 0.1902x - 6.8814$ |
| | | | S | $y = 6.2571x + 12.339$ |
| | | Curve | B | $y = 0.0219x^2 - 5.0794x + 309.18$ |
| | | | Cb | $y = 0.2955x^2 - 66.097x + 3710.7$ |
| | | | S | $y = -609.78x^2 + 434.64x - 62.296$ |
| | | Multiple regression | | $y = -0.4596x_1 + 1.79038x_2 - 1.9186x_3 - 122.0831$ |
| | After meal | Linear | B | $y = 0.1146x + 0.1397$ |
| | | | Cb | $y = 0.0954x + 3.8851$ |
| | | | S | $y = -10.428x + 18.267$ |
| | | Curve | B | $y = 0.0021x^2 - 0.3669x + 29.166$ |
| | | | Cb | $y = 0.2134x^2 - 47.52x + 2659.2$ |
| | | | S | $y = 165.47x^2 - 128.35x + 39.171$ |
| | | Multiple regression | | $y = 0.14610x_1 + 0.0410x_2 + 15.6741x_3 - 12.3707$ |
| Dinner | Before meal | Linear | B | $y = 0.0967x + 3.108$ |
| | | | Cb | $y = 0.9546x - 92.502$ |
| | | | S | $y = -27.725x + 23.969$ |
| | | Curve | B | $y = 0.0056x^2 - 1.2272x + 81.184$ |
| | | | Cb | $y = 0.2463x^2 - 54.448x + 3022.7$ |
| | | | S | $y = 514.57x^2 - 361.36x + 77.5$ |
| | | Multiple regression | | $y = 0.10264x_1 + 0.8806x_2 + 4.3424x_3 - 88.8056$ |
| | After meal | Linear | B | $y = 0.0419x + 8.902$ |
| | | | Cb | $y = 0.3592x - 26.605$ |
| | | | S | $y = -8.8817x + 16.746$ |
| | | Curve | B | $y = 0.0091x^2 - 2.0119x + 134.46$ |
| | | | Cb | $y = 0.0851^2 - 18.132x + 1055$ |
| | | | S | $y = 1298.9x^2 + 8551.83x - 124.9$ |
| | | Multiple regression | | $y = 0.0159x_1 + 0.4075x_2 + 7.0921x_3 - 36.4001$ | where B is the average of blue color values, Cb is the average of Cb color values, and S is the average saturation. In each regression analysis formula, x is the value of data used to estimate hemoglobin concentration, and y is hemoglobin concentration. In the multiple regression formula, $x^1$ is the average of blue color values, $x^2$ is the average of Cb color values, and $x^3$ is the average saturation.

A method of deriving the regression analysis formula for estimating the first hemoglobin concentration will be described later with reference to FIG. 3.

In some embodiments, the skin image analysis part 220 may estimate hemoglobin concentration by using the first skin image regression analysis formula and then improve the estimated hemoglobin concentration by introducing the estimated hemoglobin concentration into a regression analysis formula for estimating a second hemoglobin concentration.

In this instance, the regression analysis formula for estimating the second hemoglobin concentration may include a plurality of regression analysis formulae, and the skin image analysis part 200 may improve hemoglobin concentration by using a regression analysis formula for the type of the regression analysis formula for estimating the first hemoglobin concentration used to estimate hemoglobin concentration, among the plurality of regression analysis formulae.

A method of deriving the regression analysis formula for estimating the second hemoglobin concentration will be described later with reference to FIG. 4.

Table 2 below shows the error between hemoglobin concentration estimates the skin image analysis part 220 obtained using skin images and actual measurements of hemoglobin concentration.

TABLE 2

| Classification | Regression line | | | Regression curve | | | Multiple regression |
|---|---|---|---|---|---|---|---|
| | Blue | Cb | S | Blue | Cb | S | B-Cb-S |
| Before breakfast | 2.0304% | 2.8857% | 3.1129% | 3.6827% | 3.6698% | 2.7752% | 1.8967% |
| After breakfast | 4.1044% | 7.8346% | 7.5771% | 3.3322% | 5.6029% | 7.6875% | 3.7794% |
| Before lunch | 2.8014% | 2.9581% | 2.9172% | 3.7177% | 3.3161% | 0.1746% | 3.1568% |
| After lunch | 8.4275% | 6.7675% | 6.8313% | 4.3438% | 6.3806% | 6.5622% | 3.3539% |
| Before dinner | 5.7189% | 4.1052% | 3.6364% | 4.1855% | 4.0170% | 2.4947% | 3.2122% |
| After dinner | 4.7215% | 3.4420% | 4.9000% | 4.3732% | 2.3896% | 4.0181% | 3.3346% |
| Night | 3.5277% | 2.1866% | 3.2409% | 3.4137% | 3.7198% | 1.1455% | 2.0365% |
| Percent average error | | | | | | | 2.97% |

As can be seen from Table 2, it was found that, when the skin image analysis part 220 estimated hemoglobin concentration based on skin images, the hemoglobin concentration estimates showed an error of about 3% on average. Consequently, the skin image analysis allowed easy estimation of hemoglobin concentration with relatively high accuracy.

If the estimation method selection part 210 selects the health information and body information analysis, the health information and body information analysis part 230 may estimate the hemoglobin concentration of a person based on the person's input health information and body information.

More specifically, the health information and body information analysis part 230 may estimate hemoglobin concentration by introducing health information and body information into a health information regression analysis formula.

In this instance, the health information and body information analysis part 230 may determine whether to classify the health information and the body information and a classification criterion, according to the user's input. For example, the health information and the body information may be classified according to sex, smoking status, and age range. The health information and the body information may be classified into male and female according to sex, classified into smokers, non-smokers, and former smokers according to smoking status, and classified into young adult (ages 19~29), early middle-aged (ages 30~49), late middle-aged (ages 50~64), and elderly (ages 65+) according to age range.

That is, the sex, age, and smoking status parameters may be used to classify the health information and the body information, and the other parameters may be used as variables (independent variables) within the health information regression analysis formula.

The health information regression analysis formula may include a plurality of regression analysis formulae, and the health information and body information analysis part 230 may determine which regression analysis formula to use in estimating hemoglobin concentration, among the plurality of regression analysis formulae, based on whether the health information and the body information are classified or not and a classification criterion.

For example, in a case where the health information and the body information are classified, the health information and body information analysis part 230 may estimate hemoglobin concentration by using a regression analysis formula for all subjects. On the other hand, in a case where the health information and the body information are classified according to sex and a subject is male, the health information and body information analysis part 230 may estimate his hemoglobin concentration by using a male regression analysis formula.

Table 3 below shows an example of regression analysis formulae included in the health information regression analysis formula.

TABLE 3

| Category | | Multiple regression formula |
|---|---|---|
| Total number of people | | $y = 0.0705x_1 + 0.0013x_2 + 0.0083x_3 + 0.0149x_4 + 0.0016x_5 + 0.0219x_6 + 0.0143x_7 - 0.3892$ |
| Sex | Male | $y = 0.0128x_1 + 0.023x_2 - 0.0241x_3 + 0.01x_4 + 0.0016x_5 + 0.0159x_6 + 0.0048x_7 + 11.7788$ |
| | Female | $y = 0.0051x_1 + 0.0024x_2 - 0.0037x_3 + 0.00102x_4 + 0.0007x_5 + 0.015x_6 + 0.0052x_7 + 11.1864$ |
| Smoking status | Smoker | $y = 0.0512x_1 + 0.0021x_2 + 0.0075x_3 + 0.0148x_4 + 0.0011x_5 + 0.0238x_6 + 0.0125x_7 + 1.037$ |
| | Non-smoker | $y = 0.0306x_1 + 0.013x_2 - 0.0061x_3 + 0.0158x_4 + 0.0015x_5 + 0.0207x_6 + 0.0061x_7 + 7.1665$ |
| | Former smoker | $y = 0.0371x_1 + 0.0113x_2 - 0.0038x_3 + 0.012x_4 + 0.0014x_5 + 0.0192x_6 + 0.0055x_7 + 6.5948$ |
| Age range | Young adult (Ages 19~29) | $y = 0.0732x_1 + 0.0063x_2 + 0.0192x_3 + 0.0192x_4 + 0.0188x_5 + 0.0021x_6 - 0.0238x_7 - 1.328$ |
| | Early middle-aged (Ages 30~49) | $y = 0.0774x_1 - 0.0076x_2 + 0.0175x_3 + 0.0164x_4 + 0.0021x_5 + 0.0257x_6 + 0.0151x_7 - 1.9572$ |
| | Late middle-aged (Ages 50~64) | $y = 0.037x_1 - 0.0048x_2 + 0.017x_3 + 0.0149x_4 + 0.0014x_5 + 0.0158x_6 + 0.014x_7 + 0.5922$ |
| | Elderly (Ages 65+) | $y = 0.0515x_1 + 0.0091x_2 + 0.0058x_3 + 0.0134x_4 + 0.0012x_5 + 0.0208x_6 + 0.0131x_7 + 2.4152$ | wherein $x_1$ is height, $x_2$ is weight, $x_3$ is waist size, $x_4$ is diastolic blood pressure, $x_5$ is triglyceride, $x_6$ is serum GOT (ALT), and $x_7$ is gamma GTP.

A method of deriving a hemoglobin concentration estimation regression analysis formula based on health information and body information will be described later with reference to FIG. 5.

Table 4 below shows the error between hemoglobin concentration estimates obtained when the health information and the body information were not classified and actual measurements of hemoglobin concentration, Table 5 below shows the error between hemoglobin concentration estimates obtained when the health information and the body information were classified according to sex and actual measurements of hemoglobin concentration, Table 6 below shows the error between hemoglobin concentration estimates obtained when the health information and the body information were classified according to smoking status and actual measurements of hemoglobin concentration, and Table 7 below shows the error between hemoglobin concentration estimates obtained when the health information and the body information were classified according to age and actual measurements of hemoglobin concentration.

TABLE 4

| | Regression line | | | | | | | |
|---|---|---|---|---|---|---|---|---|
| Classification | Height | Weight | Waist size | Diastolic blood pressure | Triglyceride | Serum GOT (ALT) | Gamma GOT | Multiple regression analysis |
| Regression analysis for all subjects | 7.313% | 7.603% | 8.271% | 8.645% | 8.633% | 8.296% | 8.105% | 6.767% |

TABLE 5

| Classification | Regression line | | | | | | | |
|---|---|---|---|---|---|---|---|---|
| | Height | Weight | Waist size | Diastolic blood pressure | Triglyceride | Serum GOT (ALT) | Gamma GOT | Multiple regression analysis |
| Regression analysis for all males | 6.027% | 5.987% | 6.086% | 6.073% | 6.056% | 6.008% | 6.049% | 5.837% |
| Regression analysis for all females | 6.409% | 6.392% | 6.396% | 6.365% | 6.387% | 6.341% | 6.362% | 6.294% |

TABLE 6

| Classification | Regression line | | | | | | | |
|---|---|---|---|---|---|---|---|---|
| | Height | Weight | Waist size | Diastolic blood pressure | Triglyceride | Serum GOT (ALT) | Gamma GOT | Multiple regression analysis |
| Regression analysis for all smokers | 7.307% | 7.419% | 7.783% | 7.883% | 7.935% | 7.691% | 7.687% | 6.882% |
| Regression analysis for all non-smokers | 6.425% | 6.385% | 6.550% | 6.562% | 6.574% | 6.464% | 6.535% | 6.126% |
| Regression analysis for all former-smokers | 6.216% | 6.199% | 6.369% | 6.449% | 6.441% | 6.324% | 6.409% | 5.953% |

TABLE 7

| Classification | Regression line | | | | | | | |
|---|---|---|---|---|---|---|---|---|
| | Height | Weight | Waist size | Diastolic blood pressure | Triglyceride | Serum GOT (ALT) | Gamma GOT | Multiple regression analysis |
| Regression analysis for all young adults | 6.998% | 7.270% | 7.577% | 8.355% | 8.409% | 7.813% | 7.843% | 6.397% |
| Regression analysis for all early middle-aged adults | 7.436% | 7.776% | 8.206% | 8.942% | 8.785% | 8.306% | 8.256% | 6.776% |
| Regression analysis for all late middle-aged adults | 6.927% | 7.199% | 7.539% | 7.860% | 7.869% | 7.781% | 7.467% | 6.547% |
| Regression analysis for all elderly people | 7.651% | 7.840% | 8.223% | 8.383% | 8.417% | 8.207% | 8.095% | 7.345% |

As can be seen from Tables 4 to 7, it was found that, when the health information analysis and body information analysis part 230 estimated hemoglobin concentration based on body information and health information, the hemoglobin concentration estimates showed an error of about 6 to 7% on average. Consequently, the health information analysis allowed easy estimation of hemoglobin concentration with relatively high accuracy.

If the estimation method selection part 210 selects the skin image and sex-based analysis, the skin image analysis part 220 may estimate the hemoglobin concentration of a person based on the person's input skin image and sex.

The skin image analysis part 220 may estimate hemoglobin concentration by introducing at least one of the sex of the person, the average of blue color values, the average of Cb color values, and the average saturation into a sex regression analysis formula.

In this instance, the sex regression analysis formula may include a plurality of regression analysis formulae, and the skin image analysis part 220 may determine which regression analysis formula to use in estimating hemoglobin concentration, among the plurality of regression analysis formulae, based on which type of data is used in estimating hemoglobin concentration, among the average of blue color values, the average of Cb color values, and the average saturation, what sex the person is, and the type of regression analysis formula.

For example, it can be assumed that, in the case of a male subject, the average of blue color values and a linear regression formula as a regression analysis formula may be used. In this case, the skin image analysis part 220 may estimate hemoglobin concentration by using a male-blue linear regression formula. On the other hand, it can be assumed that, in the case of a female subject, the average of Cb color values and a curve regression formula as a regression analysis formula may be used. In this case, the skin image analysis part 220 may estimate hemoglobin concentration by using a female-Cb curve regression formula.

Table 8 below shows an example of regression analysis formulae included in the sex regression analysis formula.

TABLE 8

| Classification | | | Regression analysis formula |
|---|---|---|---|
| Male | Linear | B | y = 0.0113x + 14.534 |
| | | Cb | y = −0.3295x + 53.013 |
| | | S | y = 4.1481x + 14.532 |
| | Curve | B | y = 0.001$x^2$ − 0.2494x + 31.392 |
| | | Cb | y = −0.0083$x^2$ + 1.5363x − 52.151 |
| | | S | y = 217.63$x^2$ − 139.51x + 38.13 |
| | Multiple regression | | y = 0.03098$x_1$ − 0.3503$x_2$ + 5.11125$x_3$ + 49.8068 |
| Female | Linear | B | y = −0.0098x + 14.232 |
| | | Cb | y = 0.0259x + 10.009 |
| | | S | y = −0.8349x + 13.21 |
| | Curve | B | y = −0.0021$x^2$ + 0.5542x − 23.947 |
| | | Cb | y = 0.0594$x^2$ − 13.38x + 766.009 |
| | | S | y = −535.69$x^2$ + 347.49x − 43.028 |
| | Multiple regression | | y = −0.1765$x_1$ − 0.4323$x_2$ − 77.132$x_3$ + 110.478 | where B is the average of blue color values, Cb is the average of Cb color values, and S is the average saturation. In each regression analysis formula, x is the value of data used to estimate hemoglobin concentration, and y is hemoglobin concentration. In the multiple regression formula, $x^1$ is the average of blue color values, $x^2$ is the average of Cb color values, and $x^3$ is the average saturation.

Table 9 below shows the error between hemoglobin concentration estimates the skin image analysis part 220 obtained by the sex-based analysis and actual measurements of hemoglobin concentration.

TABLE 9

| | Regression line | | | Regression curve | | | Multiple regression analysis |
|---|---|---|---|---|---|---|---|
| Classification | B | Cb | S | B | Cb | S | (B-Cb-S) |
| Regression analysis for all male subjects | 4.5722% | 4.1803% | 4.5762% | 4.3736% | 3.9452% | 4.4925% | 3.9416% |
| Regression analysis for all female subjects | 4.0971% | 4.6378% | 4.5960% | 5.0641% | 4.0914% | 4.1317% | 2.6146% |

As can be seen from Table 9, it was found that, when the skin image analysis part 220 estimated hemoglobin concentration based on skin images and sex, the hemoglobin concentration estimates showed a minimum error of about 2.6% and a maximum error of about 5%. Consequently, the sex-based analysis allowed easy estimation of hemoglobin concentration with relatively high accuracy.

If the estimation method selection part 210 selects the integrated analysis, the integrated analysis part 240 may estimate the hemoglobin concentration of a person based on two or more of skin image, sex, health information, and body information.

More specifically, the user may select two or more types of data for use in estimating hemoglobin concentration. The integrated analysis part 240 may estimate an integrated hemoglobin concentration by calculating a weighted sum of hemoglobin concentrations estimated based on each of the selected data. The integrated analysis part 240 may estimate an integrated hemoglobin concentration by applying a mapping function of hemoglobin concentrations estimated based on each of the selected data.

In this instance, the weighting ratio may be preset, or may be entered by the user in the process of estimating the integrated hemoglobin concentration.

For example, if skin image and health information are selected, the skin image analysis part 220 may estimate hemoglobin concentration based on the skin image, and the health information and body information analysis part 230 may estimate hemoglobin concentration based on the health information. The integrated analysis part 240 may estimate the integrated hemoglobin concentration by calculating a weighted sum of a hemoglobin concentration estimated by the skin image analysis part 220 and a hemoglobin concentration estimated by the health information and body information analysis part 230. For example, the integrated analysis part 240 may estimate the integrated hemoglobin concentration by multiplying the hemoglobin concentration estimated by the skin image analysis part 220 by 0.6 and multiplying the hemoglobin concentration estimated by the health information and body information analysis part 230 by 0.4 and then adding the products together.

The output part 250 may output a hemoglobin concentration estimated by any of the skin image analysis part 220, the health information and body information analysis part 230, and the integrated analysis part 240.

Moreover, in some embodiments, the output part 250 may output a degree of risk, a method of hemoglobin control, etc., in addition to the hemoglobin concentration or in place of the hemoglobin concentration.

Table 10 below shows an example of diagnostic criteria for hemoglobin the output part 250 uses to output a degree of risk, a method of hemoglobin control, etc.

TABLE 10

| | Diagnostic criteria for hemoglobin (Hb) | | |
|---|---|---|---|
| Classification | Low | Normal | High |
| Male | Hb < 13 g/dl | 13.0 g/dl ≤ Hb ≤ 17.0 g/dl | 17 g/dl < Hb |
| Female | Hb < 12 g/dl | 12.0 g/dl ≤ Hb ≤ 16.0 g/dl | 17 g/dl < Hb |

For example, if the hemoglobin concentration is estimated at 8 g/dL or below, the output part 250 may present a degree of risk corresponding to bleeding. If the hemoglobin concentration is estimated at 8 to 12 g/dL, this may suggest anemia. The output part 250 may present a recommendation to eat foods rich in iron (or iron supplements), such as beef, seaweeds, leaf vegetables, milk, and eggs as a way to control hemoglobin against anemia.

Figure 3:
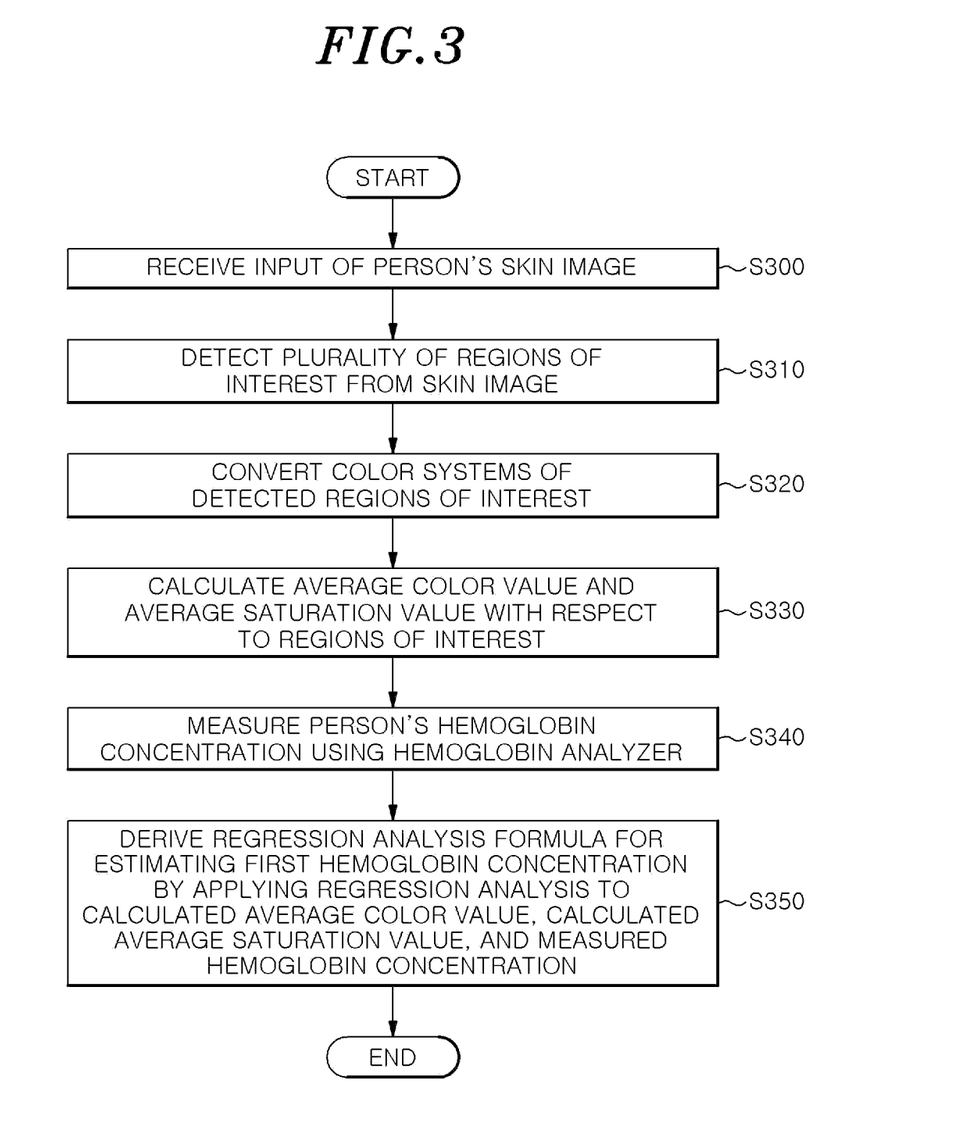
FIG. 3 is a flowchart showing a method of deriving a regression analysis formula for estimating a first hemoglobin concentration according to an embodiment of the present disclosure

FIG. 3 is a flowchart showing a method of deriving a regression analysis formula for estimating a first hemoglobin concentration according to an embodiment of the present disclosure.

Referring to FIGS. 2 and 3, when a person's skin image is inputted in order to derive a regression analysis formula for estimating a first hemoglobin concentration (S300), a plurality of regions of interest may be detected from the skin image (S310), the color systems of the detected regions of interest may be converted (S320), and the average of blue color values, the average of Cb color values, and the average saturation may be calculated with respect to the regions of interest (S330).

Also, the hemoglobin concentration of the person may be measured using a hemoglobin analyzer (S340).

The regression analysis formula for estimating the first hemoglobin concentration may be derived by applying regression analysis to the calculated average of blue color values, the calculated average of Cb color values, the calculated average saturation, and the measured hemoglobin concentration (S350).

Figure 4:
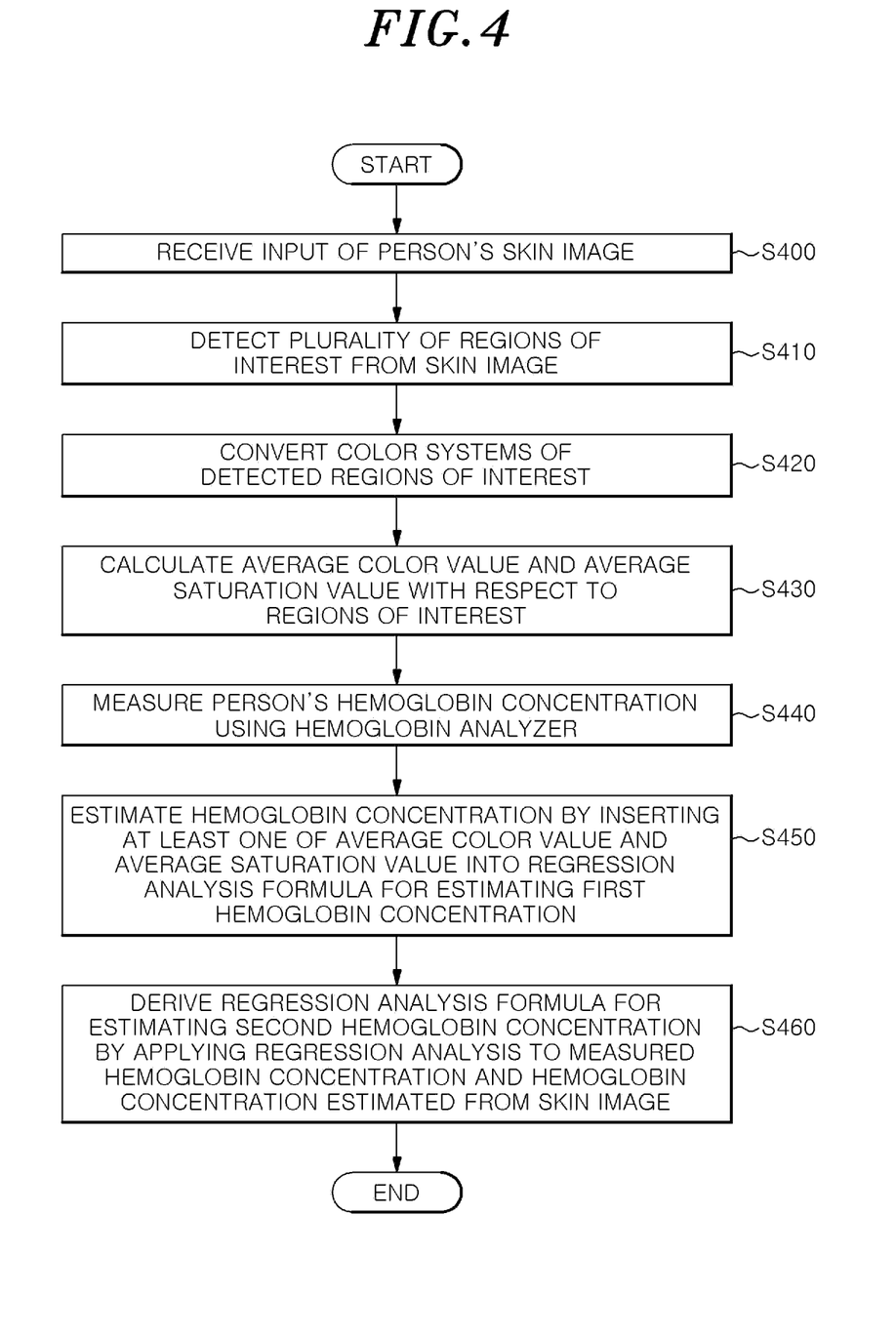
FIG. 4 is a flowchart showing a method of deriving a regression analysis formula for estimating a second hemoglobin concentration according to an embodiment of the present disclosure.

FIG. 4 is a flowchart showing a method of deriving a regression analysis formula for estimating a second hemoglobin concentration according to an embodiment of the present disclosure.

Referring to FIGS. 2 and 4, when a person's skin image is inputted (S400), a plurality of regions of interest may be detected from the skin image (S410), the color systems of the detected regions of interest may be converted (S420), and the average of blue color values, the average of Cb color values, and the average saturation may be calculated with respect to the regions of interest (S430).

Also, the hemoglobin concentration of the person may be measured using a hemoglobin analyzer (S440).

The hemoglobin concentration may be estimated by inserting at least one of the calculated average of blue color values, the calculated average of Cb color values, and the calculated average saturation into the regression analysis formula for estimating the first hemoglobin concentration (S450).

The regression analysis formula for estimating the second hemoglobin concentration may be derived by applying regression analysis to the measured hemoglobin concentration and the hemoglobin concentration estimated from the skin image (S460).

Figure 5:
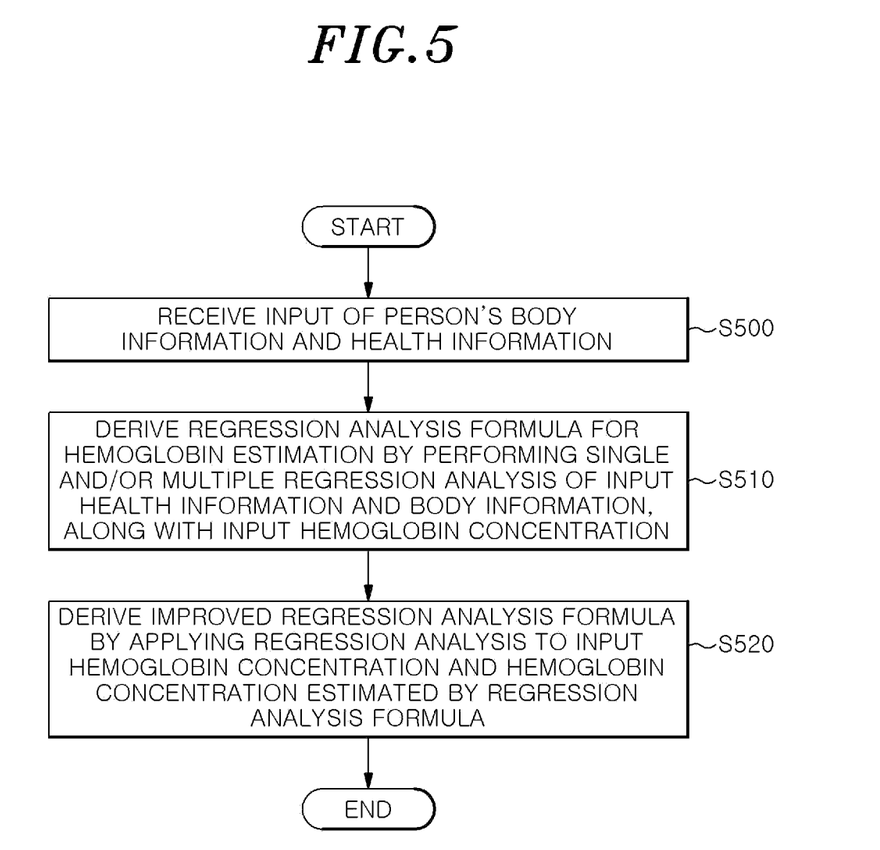
FIG. 5 is a flowchart showing a method of deriving a health information and body information-based regression analysis formula using a person's health information and body information according to an embodiment of the present disclosure.

FIG. 5 is a flowchart showing a method of deriving a health information and body information-based regression analysis formula using a person's health information and body information according to an embodiment of the present disclosure.

Referring to FIGS. 2 and 5, a person's health information and body information may be inputted in order to derive a health information and body information-based regression analysis formula (S500).

A regression analysis formula for hemoglobin estimation may be derived by performing a single and/or multiple regression analysis of the input health information (in particular, diastolic blood pressure, triglyceride, serum GOT (ALT), gamma GTP) and the input body information (e.g., height, weight, and waist size), along with an input hemoglobin concentration (S510).

An improved regression analysis formula for estimating hemoglobin concentration may be derived by applying regression analysis to the input hemoglobin concentration and the hemoglobin concentration estimated by the derived regression analysis formula (S520).

Figure 6:
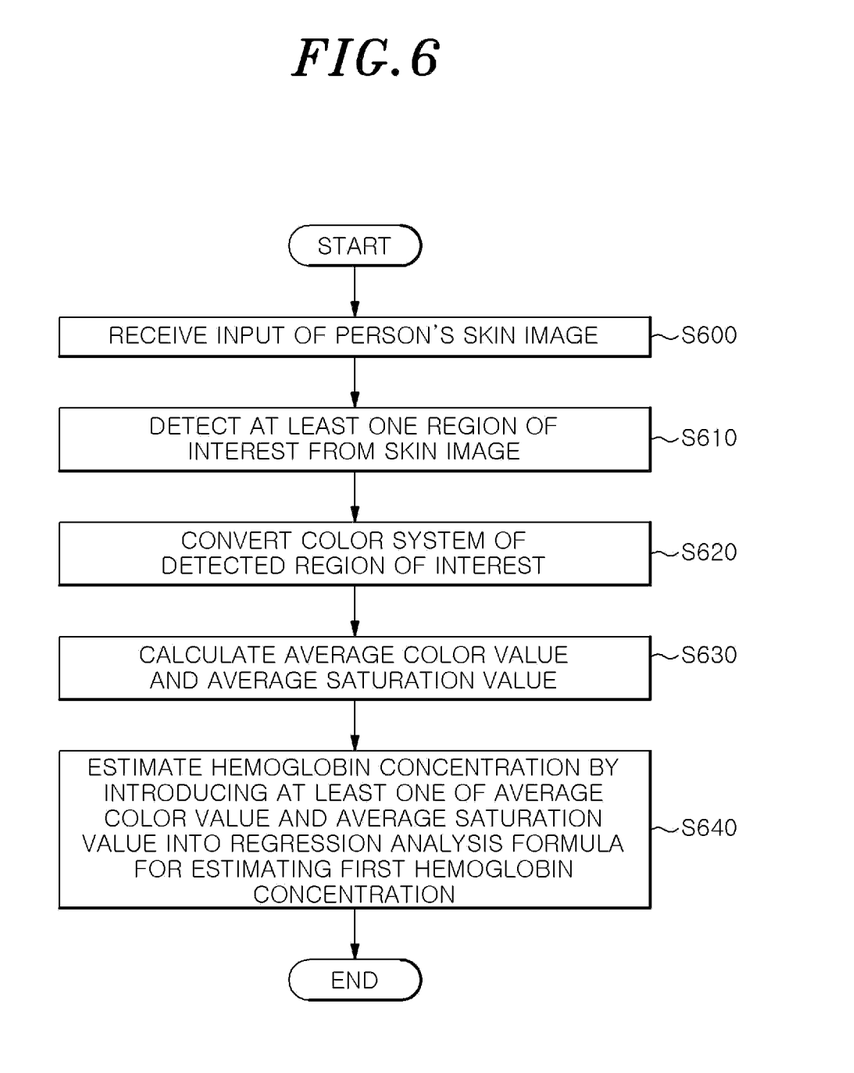
FIG. 6 is a flowchart showing a method of estimating hemoglobin concentration using skin image according to an embodiment of the present disclosure.

FIG. 6 is a flowchart showing a method of estimating hemoglobin concentration using skin image according to an embodiment of the present disclosure.

Referring to FIGS. 2 to 6, when a person's skin image is inputted (S600), the skin image analysis part 220 may detect at least one region of interest from the skin image (S610).

Afterwards, the skin image analysis part 220 may convert the color system of the detected region of interest (S620), and calculate the average of blue color values in the RGB color system, the average of Cb color values, and the average saturation (S630).

The skin image analysis part 220 may estimate hemoglobin concentration by introducing at least one of the average of blue color values, the average of Cb color values, and the average saturation into a regression analysis formula for estimating a first hemoglobin concentration (S640).

Also, the skin image analysis part 220 may improve the estimated hemoglobin concentration by introducing the estimated hemoglobin concentration into a regression analysis formula for estimating a second hemoglobin concentration (S650).

Figure 7:
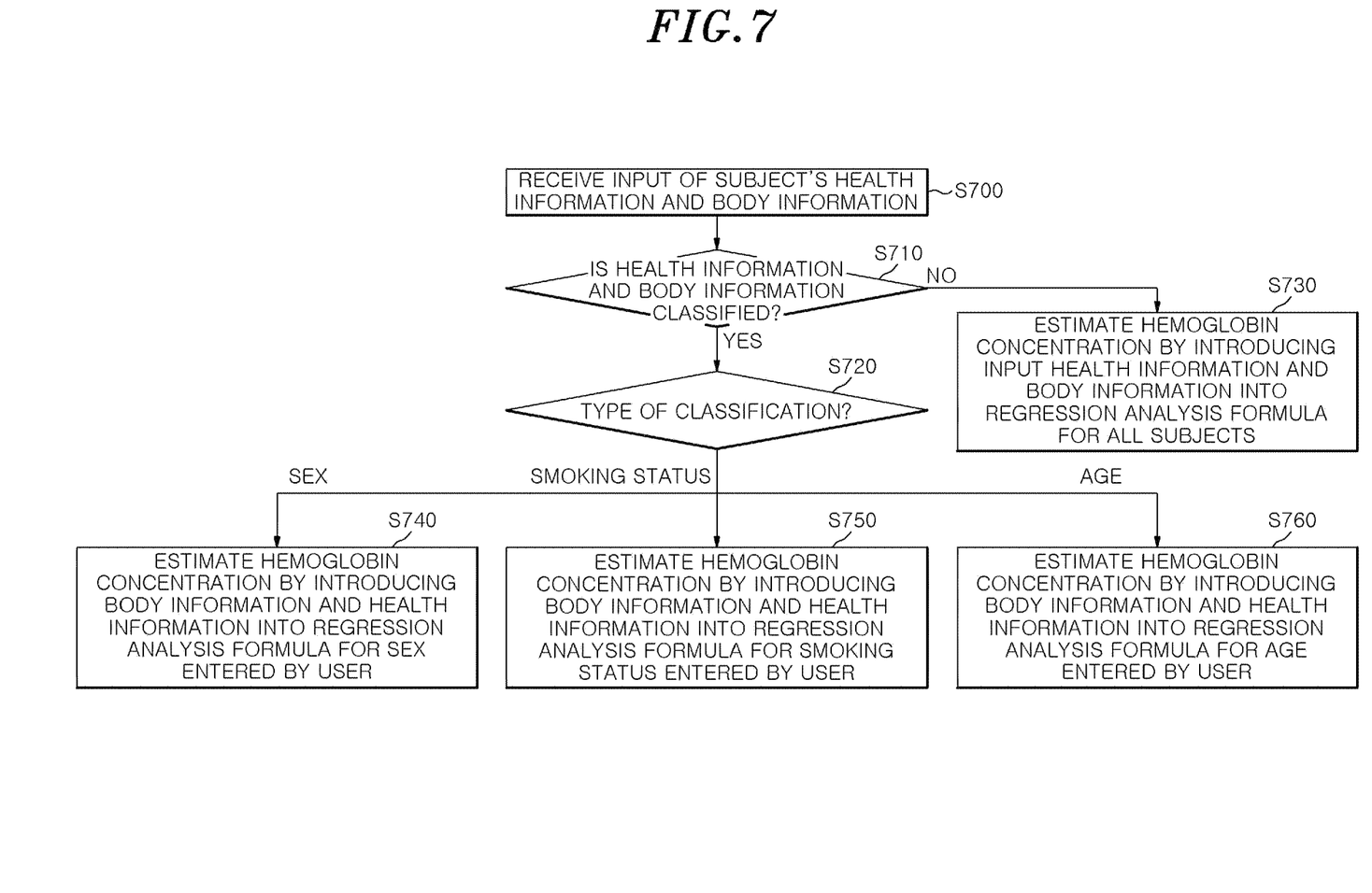
FIG. 7 is a flowchart showing a method of estimating hemoglobin concentration using health information and body information according to an embodiment of the present disclosure.

FIG. 7 is a flowchart showing a method of estimating hemoglobin concentration using health information and body information according to an embodiment of the present disclosure.

Referring to FIGS. 2 to 7, the health information and body information analysis part 230 may receive an input of a subject's health information and body information (S700).

Afterwards, the health information and body information analysis part 230 may determine whether to classify the health information and the body information (S710) and a classification criterion, according to the user's input (S720).

In a case where the health information and the body information are not classified ("NO" in S710), the health information and body information analysis part 230 may estimate hemoglobin concentration by introducing the input health information and body information into a regression analysis formula for all subjects (S730).

On the other hand, in a case where the health information and the body information are classified according to sex ("Yes" in S710 and "Sex" in S720), the health information and body information analysis part 230 may estimate hemoglobin concentration by introducing the health information and body information into a regression analysis formula for the sex entered by the user.

Moreover, in a case where the health information and the body information are classified according to smoking status ("Yes" in S710 and "Smoking status" in S720), the health information and body information analysis part 230 may estimate hemoglobin concentration by introducing the health information and body information into a regression analysis formula for the smoking status entered by the user (S750).

In addition, in a case where the health information and the body information are classified according to age ("Yes" in S710 and "Age" in S720), the health information and body information analysis part 230 may estimate hemoglobin concentration by introducing the health information and body information into a regression analysis formula for the age entered by the user (S760).

According to embodiments of the present disclosure, the present disclosure allows easy estimation of hemoglobin concentration with high accuracy, by estimating hemoglobin concentration using skin image or health information and body information.

Combinations of steps in each flowchart attached to the present disclosure may be executed by computer program instructions. Since the computer program instructions can be mounted on a processor of a general-purpose computer, a special purpose computer, or other programmable data processing equipment, the instructions executed by the processor of the computer or other programmable data processing equipment create a means for performing the functions described in each step of the flowchart. The computer program instructions can also be stored on a computer-usable or computer-readable storage medium which can be directed to a computer or other programmable data processing equipment to implement a function in a specific manner. Accordingly, the instructions stored on the computer-usable or computer-readable recording medium can also produce an article of manufacture containing an instruction means which performs the functions described in each step of the flowchart. The computer program instructions can also be mounted on a computer or other programmable data processing equipment. Accordingly, a series of operational steps are performed on a computer or other programmable data processing equipment to create a computer-executable process, and it is also possible for instructions to perform a computer or other programmable data processing equipment to provide steps for performing the functions described in each step of the flowchart. In addition, each step may represent a module, a segment, or a portion of codes which contains one or more executable instructions for executing the specified logical function(s). It should also be noted that in some alternative embodiments, the functions mentioned in the steps may occur out of order. For example, two steps illustrated in succession may in fact be performed substantially simultaneously, or the steps may sometimes be performed in a reverse order depending on the corresponding function.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. A method of estimating hemoglobin concentration, comprising:
    receiving a skin image of a subject;
    upon receiving the skin image, detecting from the skin image at least one region of interest including a body region of the subject where veins are visible;
    converting color space of the at least one region of interest; and
    calculating an average color value and an average saturation value with respect to the at least one region of interest;
    determining a formula into which the skin image is introduced; and
    estimating a hemoglobin concentration of the subject by introducing the skin image into the determined formula,
    wherein the estimating the hemoglobin concentration of the subject including estimating the hemoglobin concentration by introducing at least one of the average color value and the average saturation value into the determined formula.

2. The method of claim 1, wherein the skin image includes an image captured within a body region of the subject where veins are visible.

3. The method of claim 1, further comprising, upon receiving the skin image, detecting from the skin image at least one region of interest including a body region of the subject where veins are visible,
    wherein the estimating the hemoglobin concentration of the subject includes estimating the hemoglobin concentration of the subject by introducing the at least one region of interest into the determined formula.

4. The method of claim 1, further comprising receiving at least one of health information and body information of the subject,
    wherein the determining the formula into which the skin image is introduced includes determining the formula by using at least one of the skin image and the health information and body information, and
    the estimating the hemoglobin concentration of the subject includes estimating the hemoglobin concentration by introducing at least one of the skin image and the health information and body information into the determined formula.

5. The method of claim 4, wherein the estimating the hemoglobin concentration of the subject includes estimating the hemoglobin concentration by determining whether to classify the health information and the body information and introducing the health information and the body information into a formula corresponding to a classification criterion.

6. The method of claim 5, wherein the estimating the hemoglobin concentration of the subject includes, in a case where the health information and the body information are not classified, estimating the hemoglobin concentration by introducing the health information and the body information into a formula obtained based on subjects including the subject.

7. The method of claim 5, wherein the estimating the hemoglobin concentration of the subject includes, in a case where the health information and the body information are classified according to either the sex, smoking status, or age range indicated in the health information or the body information, estimating the hemoglobin concentration of the subject by introducing the health information and the body information into a formula for the indicated sex, smoking status, or age range.

8. The method of claim 4, wherein the estimating the hemoglobin concentration of the subject includes:
    estimating a first hemoglobin concentration by introducing the skin image into a first hemoglobin concentration estimation formula corresponding to the skin image;
    estimating a second hemoglobin concentration by introducing the first hemoglobin concentration into a second hemoglobin concentration estimation formula for the skin image;
    estimating a third hemoglobin concentration by introducing the health information and the body information into a health information and body information-based hemoglobin concentration estimation formula corresponding to the health information and the body information; and estimating an integrated hemoglobin concentration by calculating a weighted sum of two or more of the first hemoglobin concentration, the second hemoglobin concentration, and the third hemoglobin concentration.

9. An apparatus of estimating hemoglobin concentration, comprising:
a memory storing a hemoglobin concentration estimation program; and
a processor configured to execute the hemoglobin concentration estimation program by loading the hemoglobin concentration estimation program from the memory,
wherein the processor executes the hemoglobin concentration estimation program configured to receive a skin image of a subject,
wherein the processor is further configured to:
upon receiving the skin image, detect from the skin image at least one region of interest including a body region of the subject where veins are visible,
convert color space of the at least one region of interest,
calculate an average color value and an average saturation value with respect to the at least one region of interest,
determine a formula into which the skin image is introduced, and
estimate the hemoglobin concentration of the subject by introducing the skin image into the formula, and
estimate the hemoglobin concentration of the subject by introducing at least one of the average color value and the average saturation value into the determined formula.

10. The apparatus of claim 9, wherein, upon receiving the skin image, the processor is configured to detect from the skin image at least one region of interest including a body region of the subject where veins are visible.

11. The apparatus of claim 10, wherein the processor is configured to estimate the hemoglobin concentration of the subject by introducing the at least one region of interest into the determined formula.

12. The apparatus of claim 10, wherein the processor is configured to:
receive at least one of health information and body information,
determine the formula by using at least one of the skin image and the health information and body information, and
estimate the hemoglobin concentration of the subject by introducing at least one of the skin image and the health information and body information into the determined formula.

13. The method of claim 12, wherein the processor is configured to estimate the hemoglobin concentration of the subject by determining whether to classify the health information and the body information and introducing the health information and the body information into a formula corresponding to a classification criterion.

14. The apparatus of claim 13, wherein, in a case where the health information and the body information are classified according to either the sex, smoking status, or age range indicated in the health information or the body information, the processor is configured to estimate the hemoglobin concentration by introducing the health information and the body information into a formula for the indicated sex, smoking status, or age range.

15. A non-transitory computer-readable recording medium storing a computer program, which comprises instructions configured for a processor to execute a method of estimating hemoglobin concentration, the method comprising:
receiving a skin image;
upon receiving the skin image, detecting from the skin image at least one region of interest including a body region of the subject where veins are visible;
converting color space of the at least one region of interest;
calculating an average color value and an average saturation value with respect to the at least one region of interest;
determining a formula into which the skin image is introduced; and
estimating the hemoglobin concentration of the subject by introducing the skin image into the determined formula,
wherein the estimating the hemoglobin concentration of the subject includes estimating the hemoglobin concentration by introducing at least one of the average color value and the average saturation value into the determined formula.

16. The non-transitory computer-readable recording medium of claim 15, comprising instructions configured to, upon receiving the skin image, detect from the skin image at least one region of interest comprising a body region of the subject where veins are visible.

17. The non-transitory computer-readable recording medium of claim 16, comprising instructions configured to estimate the hemoglobin concentration of the subject by introducing the at least one region of interest into the determined formula.

* * * * *